(12) United States Patent
Paulasaari et al.

(10) Patent No.: US 6,284,906 B1
(45) Date of Patent: Sep. 4, 2001

(54) CYCLOTRISILOXANES, NEW SILOXANE POLYMERS AND THEIR PREPARATION

(75) Inventors: Jyri Kalevi Paulasaari; William P. Weber, both of Los Angeles, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 09/612,617

(22) Filed: Jul. 6, 2000

Related U.S. Application Data

(63) Continuation of application No. 09/416,265, filed on Oct. 12, 1999, now abandoned.

(51) Int. Cl.[7] .................................................... C07F 7/08
(52) U.S. Cl. ......................... 556/451; 556/450; 556/453; 556/459; 556/460; 556/461; 528/12; 528/14
(58) Field of Search ..................................... 556/451, 450, 556/453, 459, 460, 461; 528/12, 14

(56) References Cited

U.S. PATENT DOCUMENTS

| | | | |
|---|---|---|---|
| 5,246,703 | * | 9/1993 | Durfee ................................. 556/460 |
| 5,700,899 | * | 12/1997 | Aoki et al. ......................... 528/12 X |
| 5,852,153 | * | 12/1998 | Sugo et al. .............................. 528/14 |

OTHER PUBLICATIONS

Jyri K. Paulasaari and William P. Weber, "Preparation and polymerization of 1,3,3,5,5-pentamethyl-1-(2'-perfluorophenyl-1',1',2',2'-tetrahydroethyl)cyclotrisiloxane (I). Comparison of anionic and cationic polymerization of I", 39 *Polym. Prepr.*, 583–584 (1998) (Abstract).

Jyri K. Paulasaari and William P. Weber, "Preparation and Orthogonal Polymerizations of 1–Hydrido–1–vinyldimethylsiloxy–3,3,5,5–tetramethylcyclotrisiloxane", 32 *Macromolecules* 5217–5221 (1999) (Abstract).

Jyri K. Paulasaari and William P. Weber, "Polymerizations of 1–Hydrido–1–vinyldimethylsiloxy–3,3,5,5–tetramethylcyclotrisiloxane", 40 *Polym. Prepr.* 801–802 (1999) (Abstract).

Jyri K. Paulasaari and William P. Weber, "Preparation of Highly Regular Poly(1–Hydrido–1,3,3,5,5–pentamethyltrisiloxane) and Its Chemical Modification by Hydroxsilylation", 32 *Macromolecules* 6574–6577 (1999) (Abstract).

* cited by examiner

*Primary Examiner*—Paul F. Shaver
(74) *Attorney, Agent, or Firm*—James C. Lydon

(57) ABSTRACT

This invention relates to methods for the preparation of hyperbranched siloxane polymers by anionic polymerization of a cyclotrisiloxane having the functional group Si—OH, and for the preparation of linear siloxane polymers by cationic or anionic polymerization of a cyclotrisiloxane having a vinylterminated functional group. Furthermore, this invention concerns novel cyclotrisiloxanes useful for the preparation of the aforementioned polymers.

12 Claims, No Drawings

CYCLOTRISILOXANES, NEW SILOXANE POLYMERS AND THEIR PREPARATION

This application is a continuation of application Ser. No. 09/416,265, filed Oct. 12, 1999, and now abandoned.

This invention concerns new cyclotrisiloxanes, new hyperbranched or linear siloxane polymers, and their preparation.

BACKGROUND OF THE INVENTION

The publications and other materials used herein to illuminate the background of the invention, and in particular, cases to provide additional details respecting the practice, are incorporated by reference.

Organosilicon dendritic and hyperbranched polymers are well known. The dendrimer core is usually prepared from tetraallyl- or -vinylsilane, which is then derivatized by hydrosilylation reaction (1, 2). On the other hand, hyperbranched polycarbosilanes are commonly prepared from vinyltris(dimethylsiloxy)silane via hydrosilylation reactions. Typically, 8–10 mol-% starting material cyclizes in a side reaction (3). See Scheme 1.

There are few examples of hyperbranched or dendritic polysiloxanes, eg. polymers, whose backbone consist only of —SiRR'—O— linkages. Probably the most significant paper is by Uchicda et al. (4) which describes a multistep pathway for highly regular third generation dendritic polysiloxanes with molecular weight of about 15,000 g/mol. See Scheme 2.

Rebrov (5) used a different approach. He let $MeSiCl_3$ react with three equivalents of $NaOSiMe(OEt)_2$. Ethoxy groups were then converted quantitatively into chlorines by reaction with thionyl chloride. Treatment of the resulting product again with $NaOSiMe(OEt)_2$, followed by conversion of the Si—OEt into Si—Cl groups repeatedly gave a fourth generation polymer in >75% yield. See Scheme 3.

Morikowa (6) utilized easily cleavageable Si—Ph bond in his synthesis. The core was prepared from a compound having three Si-phenyl groups which were converted into Si—Br by treatmnent of $Br_2$. Reaction with $HNMe_2$ gave Si—N functionalities, which in turn could be reacted with silanols bearing Si-phenyl groups. This cycle was repeated two times to give a $3^{rd}$ generation dendrimer in 32% yield, with a molecular weight of about 4,800 g/mol. See Scheme 4.

Scheme 1

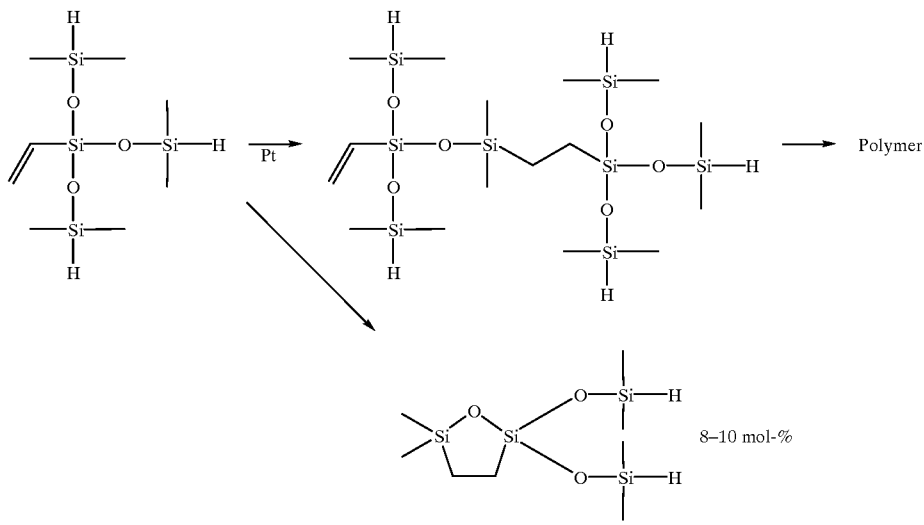

Scheme 2
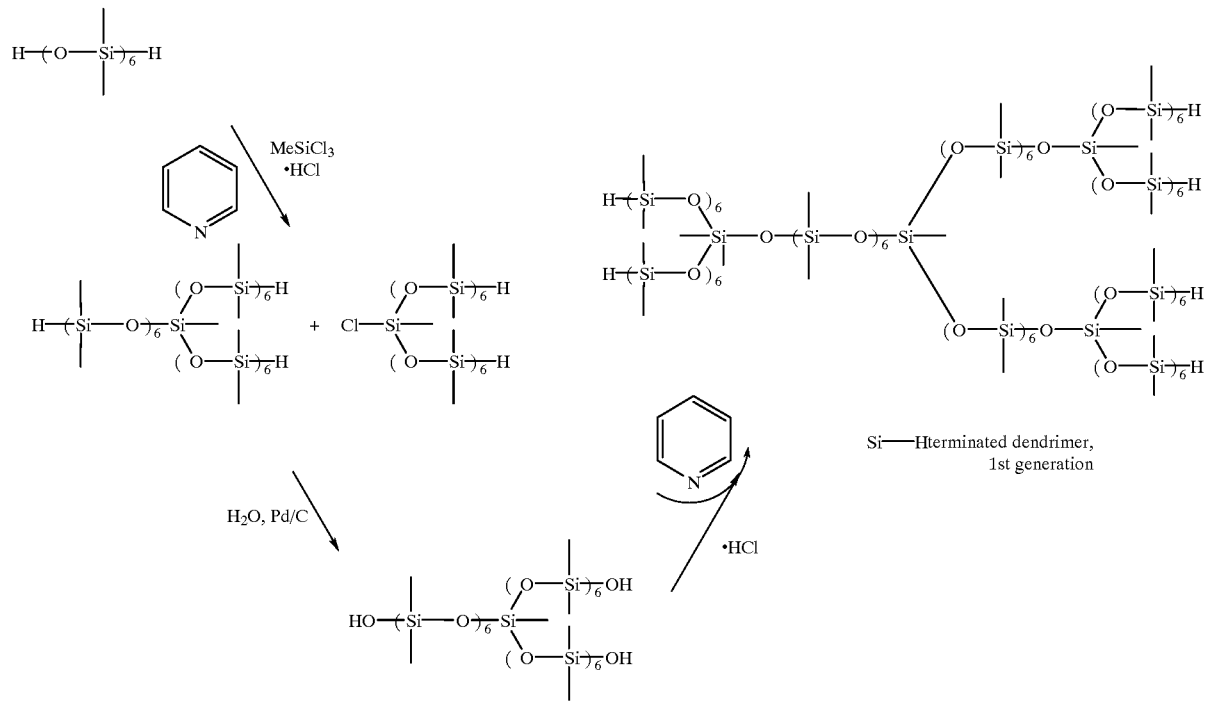
Si—H terminated dendrimer,
1st generation
-continued
Scheme 3
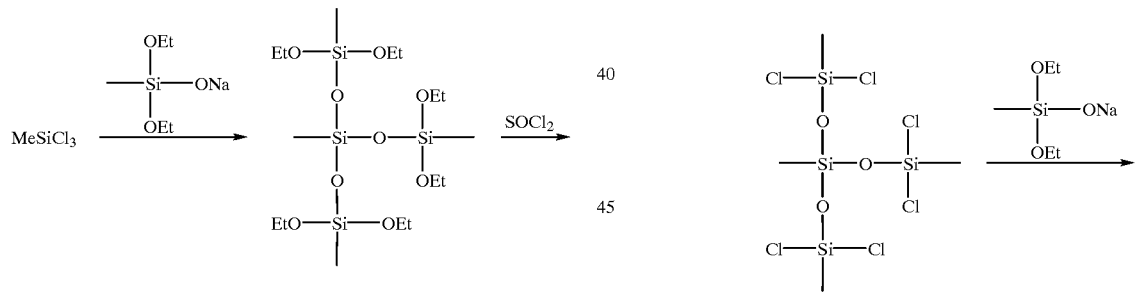

Scheme 4

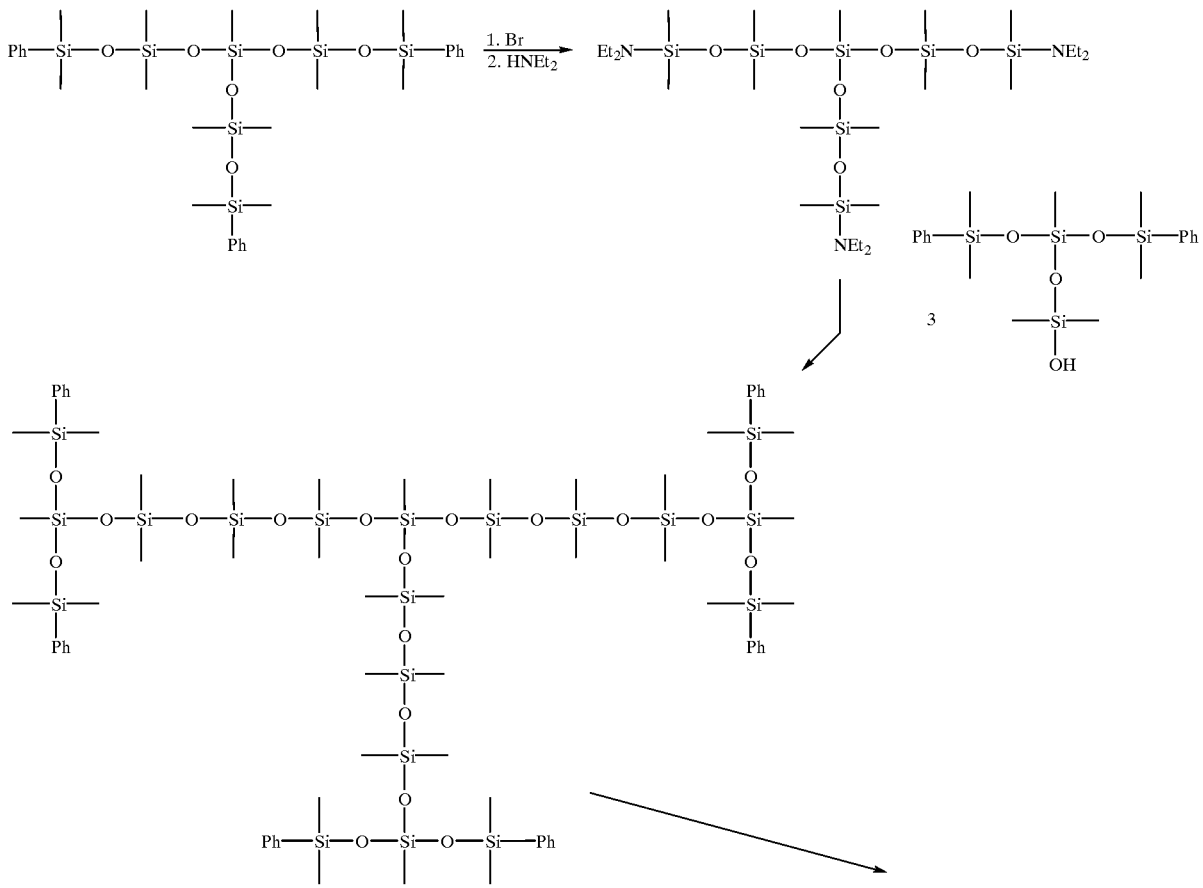

OBJECTS AND SUMMARY OF THE INVENTION

The aim of this invention is to provide convenient methods for the preparation of hyperbranched siloxane polymers by anionic polymerization of a cyclotrisiloxane having the functional group Si—OH, and for the preparation of linear siloxane polymers by cationic or anionic polymerization of a cyclotrisiloxane having a vinyl terminal functional group. A further object of this invention is to provide novel cyclotrisiloxanes useful for the preparation of the aforementioned polymers.

Thus, according to one aspect, this invention concerns a novel cyclotrisiloxane of the formula (I)

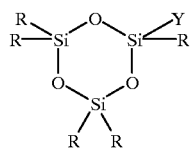

(I)

wherein Y is OSi(R)$_2$H, OSi(R)$_2$OH, or O—Si(R)$_2$—OSi(R)$_2$—CH=CH$_2$, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted.

According to another aspect, the invention concerns a method for the preparation of hyperbranched siloxane polymer, wherein a compound of formula (II)

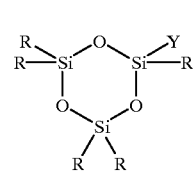

(II)

wherein Y is OH or OSi(R)$_2$OH, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted is subjected to anionic polymerization, in bulk or in a suitable solvent, e.g. TBF, to give a hyperbranched polymer, which has the formula (IIIa1, IIIa2, IIIa3) or (IIIb1, IIIb2, IIIIb3)

IIIa1

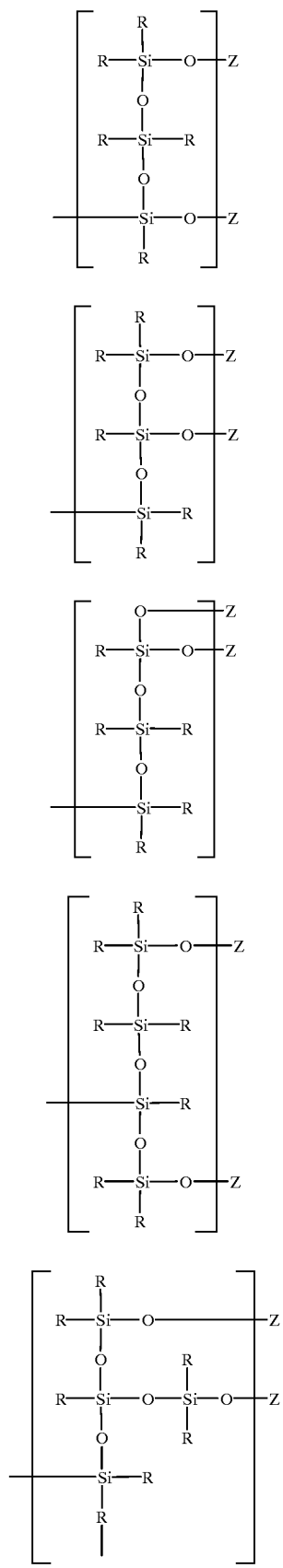

IIIa2

IIIa3

IIIb1

IIIb2

IIIb3

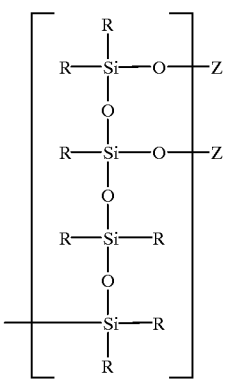

wherein the substituents R are as defined above and where each Z in IIIa1–a3 is one of the groups IIIa1–a3, and each Z in IIIb1–b3 is one of the groups IIIb1–b3, or Z is an endcapping group. Said endcapping group, which can be the same or different, can be hydrogen obtained by neutralization, or a radical derived from a halosilane or a halosiloxane, e.g. chlorosilane or chlorosiloxane, wherein said halosilane or halosiloxane can bear functional or non-functional groups. As examples of said functional or non-functional group can be mentioned hydrogen, vinyl, the substituent R as defined before, amino, alkoxy or polyalkylene oxide. The endcapping of the polymer can also be carried out by using a mixture of different compounds. By proper choice of endcapping group the surface of the polymer can be modified in desired ways.

According to a further aspect, the invention concerns a method for the preparation of a linear siloxane polymer, wherein a compound of the formula (IV)

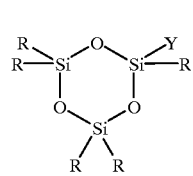

(IV)

wherein Y is $O-Si(R)_2-OSi(R)_2-CH=CH_2$, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted, is subjected to cationic or anionic polymerization to give a linear polymer, which has the formula (V)

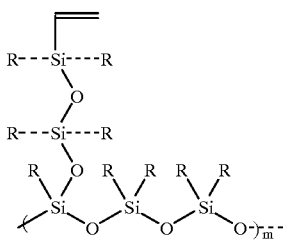

(V)

wherein the substituents R are the same as in compound (IV) and m is 3 to 9000.

The invention also concerns the novel hyperbranched or linear siloxane polymers.

DETAILED DESCRIPTION OF THE INVENTION

According to a preferred embodiment, each R-substituent in the cyclotrisiloxane of formula (I) is the same and is an alkyl of 1 to 4 carbon atoms. Most preferably, each R-substituent is methyl.

The anionic polymerization of the Si—OH functionalized cyclotrisiloxane (compound (II)) can be carried out in the presence of a lithium containing base, for example an alkyl lithium such as n-butyl lithium or triphenylmethyl lithium, or lithium diisopropyl amide. The polymerization can be carried out in bulk or in a suitable solvent. As an example of a suitable solvent can be mentioned THF.

Alternatively, the anionic polymerization can be carried out by subjecting the Si—OH functionalized cyclotrisiloxane to a catalytic amount of superbase such as a phosphazene. A particularly useful superbase is phosphazene base $P_4$-t-Bu [1-tert-Butyl-4,4,4-tris(dimethylamino)-2,2-bis[tris(dimethylamino)-phosphoranyliden-amino]-$2\lambda^5$, $4\lambda^5$-catenadi(phosphazene)].

The preparation of linear siloxane polymers can be carried out by cationic polymerization initiated by an acid such as trifluoromethane sulfonic acid (triflic acid) or by anionic polymerization initiated by bases such as dilithium diphenylsilanolate or dilithium tetramethylsiloxanediolate.

The invention will be described more in detail in the Experimental section in the following non-limiting examples.

EXPERIMENTAL

Spectroscopic Analysis $^1$H, $^{13}$C and $^{29}$Si NMR spectra were obtained on a Bruker AMX-500 MHz spectrometer operating in the FT mode. $^1$H NMR spectra were run on 5 % w/v chloroform-d solutions. Forty percent w/v solutions in acetone-$d_6$ were used to obtain $^{29}$Si and $^{13}$C NMR spectra. $^{13}$C NMR spectra were obtained with broad band proton decoupling. An inverse gate decoupling pulse sequence with a 60 sec delay was used to acquire $^{29}$Si NMR spectra. Tetramethylsilane (TMS) was used as an internal standard for $^1$H, $^{13}$C and $^{29}$Si NMR spectra.

IR spectra of neat films on NaCl plates were recorded on a Perkin Elmer Spectrum 2000 FF-IR spectrometer. GPC analysis of the molecular weight distribution of the polymers was performed on a Waters system equipped with a refractive index detector. Two 7.8 mm×300 mm Styragel columns packed with <5 μ divinylbenzene cross-linked polystyrene HR4 and HR2 in series were used for the analysis. The eluting solvent was toluene at a flow rate of 0.3 mL/min. The retention times were calibrated against known monodisperse polystyrene standards. TGA of the polymers was measured on a Shimadzu TGA-50 instrument. The temperature program was 4° C./min from 25 to 850° C.

$T_g$ of the polymer was determined by DSC on a Perkin-Elmer DSC-7. The temperature program for the analysis we begun at −150° C. The temperature was increased at a rate of 10° C./min. Light scattering CPS/MALLS was performed with a Wyatt Dawn-DSP MALLS detector, which is inserted between the GPC columns and R410 RI detector. Data were analyzed with a Wyatt Astra system. THF was used as the eluant.

All reactions were conducted in flame dried glassware under an atmosphere of argon.

EXAMPLE 1

Preparation of 1-dimethylsiloxy-1,3,3,5,5-pentamethylcyclotrisiloxane a) 1,1-Dichloro-1,3,3-trimethyldisiloxane 1,3-Dihydridotetramethyldisiloxane (57 g, 0.42 mol) and methyltrichlorosilane, (96 g, 0.64 mol) were placed into 200 mL rb flask equipped with a Teflon covered magnetic stirbar and sealed with a rubber septum. The catalyst solution (500 μL) was injected into flask at room temperature (RT). No reaction occurred. Dry HCl gas was slowly bubbled into solution. Excess pressure was relieved through a syringe needle which was attached to a drying tube which was filled with Drierite. An exothermic reaction occurred. The contents of the flask warmed to about 35° C. in 10 minutes. Addition of gaseous HCl gas was continued for 2 h. The reaction mixture was distilled through a 50 cm vacuum jacketed column which was packed with stainless steel saddles. A fraction, 33.6 g (42% yield), bp 116° C., was collected. $^1$H NMR δ: 0.32(d, 6H, J=3 Hz), 0.84(s, 3H), 4.77(septet, 1H, J=3 Hz); $^{13}$C NMR δ: −0.17, 5.97; $^{29}$Si NMR δ: −17.10 (1Si), 0.94 (1Si). IR ν: 2966, 2151, 1414, 1258, 1088, 904, 797 cm$^{-1}$.

b) Tetramethyldisiloxane-1,3-diol

The compound was prepared by the controlled hydrolysis of dimethyldichlorosilane (5).

c) 1-Dimethylsiloxy-1,3,3,5,5-pentamethylcyclotrisiloxane 1,1-Dichloro-1,3,3-trimethyldisiloxane (25.0 g, 0.13 mol) in 30 mL $Et_2O$ and tetramethyldisiloxane-1,3-diol (22.0 g, 0.13 mol) in 30 mL $Et_2O$ were added dropwise to a solution of $Et_3N$ (28.0 g, 0.28 mol) and 170 mnL $Et_2O$ over one hour at RT. After stirring for 2 h, the reaction mixture was filtered and washed with water, dilute $H_3PO_4$ solution and saturated $NaHCO_3$. It was dried over anhydrous $MgSO_4$, filtered and the volatiles were removed by evaporation under reduced pressure. Fractional distillation through a 10 cm vacuum jacketed column gave a fraction, 26.9 g (72% yield), bp 81° C. (40 mm Hg). $^1$H NMR δ: 0.09(s, 3H), 0.12(s, 6H), 0.14(s, 6H), 0.20(d, 6H, J=3 Hz), 4.75(sept., 1H, J=3 Hz). $^{13}$C NMR δ: −3.11, 0.52, 0.72, 0.82. $^{29}$Si NMR δ: −56.20(1Si), −8.50 (2Si), −5.72(1Si). IR ν: 2966, 2907, 2133, 1406, 1260, 1089, 1020, 907, 862, 810, 770, 624 cm$^{-1}$.

EXAMPLE 2

1-(Hydroxydimiethylsiloxy)-1,3,3,5,5-pentamethylcyclotrisiloxane

A homogenous solution was formed from 1-dimethylsiloxy-1,3,3,5,5-pentamethylcyclotrisiloxane obtained in Example 1(20.0 g, 70 inmol), 250 mL dioxane and 30 mL distilled water. Palladium catalyst (10% Pd/C, 0.5 g) was added to the solution in three aliquots at RT, and the system was allowed to react for 12 h. No more $H_2$ evolved when small amount of additional catalyst was added. After filtration and removal of volatiles by evaporation, fractional distillation gave a fraction, 19.6 g (66 mmol, 93% yield), bp 52° C. (0.1 mm Hg). $^1$H NMR δ: 0.10(6H), 0.11(3H), 0.12(6H), 0.15(6H), 5.15(1H). $^{13}$C NMR δ: −2.81, 0.85. $^{29}$Si NMR δ: −57.63(1Si), −12.45(1Si), −8.32(2Si). IR ν: 3339(br), 2966, 2907, 1411, 1262, 1092, 1023, 880, 867, 809, 764, 624 cm$^{-1}$.

EXAMPLE 3

1-Dimethylsiloxy-1-phenyl-3,3,5,5-tetramethylcyclotrsiloxane

The preparation was carried out according to the procedure described in Example 1 from 1-phenyl-1,1-dichloro-3,3-dimethyldisiloxane (22.0 g, 88 mmol), tetramethyldisiloxane-1,3-diol (14.56 g, 88 mmol), and $Et_3N$ (18.6 g, 184 mmol) in 210 mL diethyl ether. 13.02 g (yield 43%), bp. 86° C. (1 mm Hg). $^1$H NMR δ: 0.17(s, 6H), 0.24(s, 6H), 0.26(d, 6H, J=2.5 Hz), 4.82 (sept. 1H, J=2.5 Hz), 7.42(m, 3H), 7.65(m, 2H). $^{13}$C NMR δ: 0.80, 0.98, 1.23, 128.42, 130.86, 133.73, 134.30. $^{19}$F NMR δ: $^{29}$Si NMR δ: −70.00(1Si), −7.27(2Si), −3.90(1 Si). IR ν: 2964, 2133, 1431, 1261, 1133, 1084, 1021, 998, 902, 851, 808, 771, 699, 641 cm$^{-1}$.

EXAMPLE 4

1-(Hydroxydimethylsiloxy)-1-phenyl-3,3,5,5-tetramethylcyclotrisiloxane

The preparation was carried out according to the procedure described in Example 2 from 1-dimethylsiloxy-1-phenyl-3,3,5,5-tetramethylcyclotrisiloxane from Example 2 (8.34 g, 24 mmol), distilled water (10 mL), catalyzed by 0.4 g 10% Pd/C. 6.18 g (yield 71%), bp. 94° C. (0.2 mm Hg). $^1$H NMR δ: 0.13(s, 6H), 0.16(s, 6H), 0.23(s, 6H), 5.37(s, 1H), 7.41(m, 3H), 7.67(m, 2H). $^{13}$C NMR δ: 0.62, 0.90, 1.10, 128.31, 130.72, 134.38. $^{29}$Si NMR δ: −71.73(1Si), −11.97(1Si), −7.35(2Si). IR ν: 3392, 2964, 1595, 1431, 1262, 1133, 1189, 1020, 998, 879, 852, 808, 745,717, 699, 641, 593 cm$^{-1}$.

EXAMPLE 5

3'-Vinyl-1',1',3',3'-tetramethyldisiloxy-1,3,3,5,5-pentamethylcyclotrisiloxane

Vinyldimethylchlorosilane (4.0 g, 33 mmol) in 10 mL $Et_2O$ was added dropwise to a solution of 1-dimethylhydroxysiloxyl-1,3,3,5,5-pentamethylcyclotrisiloxane prepared in Example 2 (4.85 g, 16 mmol), 60 mL $Et_2O$ and $Et_3N$ (4.0 g, 40 mmol) at RT during 20 min. After 5 h, the reaction was filtered. The filtrate was washed with water, dilute aqueous $H_3PO_4$ and saturated $NaHCO_3$, to remove the triethylammonium chloride, dried over anhydrous $MgSO_4$ and filtered. Final product was obtained in 4.91 g (0.13 mol, yield 79%) by fractional distillation at 50° C. /(0.15 mm Hg). $^1$H NMR δ: 0.09(s, 6H), 0.11 (s, 3H), 0.13(s, 6H), 0.15(d, 6H, J=0.5 Hz), 0.17(s, 6H), 5.76(dd, 1H, J=21 and 4 Hz), 5.93(dd, 1H, J=15 and 4 Hz), 6.14(dd, 1H, J=21 and 15 Hz). $^{13}$C NMR δ: −2.73, 0.36, 0.77, 0.93, 1.07, 132.08, 139.69. $^{29}$Si NMR δ: −58.11 (1Si), −20.30(1Si), −8.40(2Si), −3.53(1Si). IR ν: 3052, 2965, 2906, 1596, 1408, 1261, 1068, 1021, 862, 839, 808, 763, 710, 625 cm$^{-1}$.

EXAMPLE 6

Preparation of a linear siloxane polymer by cationic polymerization

3'-Vinyl-1',1',3',3 '-tetramethyldisiloxyl- 1,3,3,5,5-pentamethylcyclotrisiloxane from Example 5 (1.0 g, 2.6 miol) in 250 μL of 1,1,2-trichlorotrifluoroethane was cooled to −78° C. and 5 μL trifluoromethane sulfonic acid (triflic acid) was injected into solution. Additional 1,1,2-trichlorotrifluoroethane (3×250 μL) was added when the system became too viscous to permit stirring. The reaction was quenched after 0.5 h by addition of 20 mg, 0.12 mmol hexamethyldisilazane. Polymer was precipitated three times from a mixture of $Et_2O$/MeOH, and dried under vacuum for 12 h. In this way, 0.48 g (48% yield) of polymer was obtained. $M_n/M_W$=83,900/28,300. $^1$H NMR δ: 0.08–0.18 (m, 27H), 5.75(dd, 1H, J=20.5 and 4 Hz), 5.92(dd, 1H, J=15 and 4 Hz), 6.13(dd, 1IH, J=20.5 and 15 Hz). $^{13}$C NMR δ: −2.04, −2.02, −0.39, 1.11 1.15, 1.18, 1.20, 1.23, 1.28, 131.96, 139.57. $^{29}$Si NMR δ: −67.17, −67.11, −21.93, 21.92, −21.84, −21.76, −21.75, −21.68, −21.04, −3.95, −3.94. IR ν: 3053, 2964, 2906, 1596, 1408, 1261, 1094, 1030, 956, 839, 799, 756, 707, 518 cm$^{-1}$.

EXAMPLE 7

Preparation of a linear siloxane polymer by anionic polymerization a) Initiator

Dilithium diphenylsilanolate was prepared by treatment of diphenylsilanediol with n-butyl lithium in THF. Styrene was used as an indicator (8).

b) Anionic polymerization

Initiator (22 μL,10 μmol) was injected to a solution of 3'-vinyl-1', 1',3',3'-tetramethyldisiloxyl-1,3,3,5,5-pentamethylcyclotrisiloxane from Example 5 (1.0 g, 2.6 mmol) in 250 μL THF at RT. Polymerization was carried out for 24 h, after which it was quenched with vinyldimethylchlorosilane (0.1 g, 0.8 mmol). The polymer was precipitated three times with $Et_2O$/MeOH and dried in vacuum for 10 h, yielding 0.92 g (92%) of product. $M_w/M_n$=29,100/12, 400. TGA: Decomposition begins at 425° C. At 530° C., 90% of material is left. At 655° C., half of the total weight is lost. Forty five percent residue is left at 850° C.

EXAMPLE 8

Preparation of a linear siloxane polymer by anionic polymerization using a superbase The superbase (Phosphazene Base $P_4$-t-Bu (1M in n-hexane) (2 μL, 2 μmol) was injected into solution of 3'-vinyl-1',1',3',3'-tetramethyldisiloxyl-1,3,3,5,5-pentamethylcyclotrisiloxane (1.0 g, 2.6 mmol) in 250 pL TBF at RT. After 0.5 h, reaction was quenched with dimethylvinylchlorosilane (0.1 g, 0.8 mmol). Volatiles were removed by vacuum. Reaction product was low viscous liquid, $M_w/M_n$=8700/2100.

EXAMPLE 9

Preparation of a hyperbranched polymer by anionic polymerization

The monomer (1-dimethylhydroxysiloxyl-1,3,3,5,5-pentamethylcyclotrisiloxane), 2.0 g, 6.7 mmol and THF 1.0 mL were cooled to $-9°$ C. and the base ($P_4$-t-Bu) (8 $\mu$L, 8 $\mu$mol) was injected. After 4 h, 1 mL THF, $Et_3N$ (2 mL, 7.3 mmol) and 1 mL vinyldimethylchlorosilane was added, and stirring was continued for 12 h. Polymer was extracted into hexamethyldisiloxane, washed with aq. NaCl and precipitated three times from TBF/MeOH. Yield 2.47 g (96%), $M_w/M_n$=15400/5900. $^1$H NMR δ: 0.05–0.20(m, 27H), 5.74 (dd, 0.65H, J=20.5 and 4.5 Hz), 5.76(dd, 0.35H, J=20.5 and 4.5 Hz), 5.91(dd, 0.65H, J=14 and 4.5 Hz), 5.92(dd, 0.35H, J=14 and 4.5 Hz), 6.13(dd, 0.65H, J=20.5 and 14.5 Hz), 6.13 (dd, 0.35H, 20.5 and 14.5 Hz). $^{13}$C NMR δ: −2.79, −2.11, 0.25, 0.36, 0.75–1.23(m), 131.84, 131.97, 139.27, 139.49. $^{29}$Si NMR δ: −67.27, 067.20, −67.14, −67.06, −66.20, −66.14, −66.06, −22.05, −21.97, −21.89, −21.82, −21.80, −21.76, −21.74, −21.11, −8.55, −4.00, −3.66, −3.64. IR v: 3053, 2964, 2906, 1596, 1408, 1261, 1093, 1028, 956, 839, 799, 756, 707, 519 $cm^{-1}$.

EXAMPLE 10

Preparation of a hyperbranched polymer from 1-hydroxy-1,3,3,5,5,-pentamethylcyclotrisiloxane, phenyldimethylsiloxy terminated THF (0.3 mL) and Phosphazene Base $P_4$-t-Bu Solution (10 $\mu$L, Fluka Chemie AG) were placed into a test tube equipped with a Teflon covered magnetic stirbar and sealed with a rubber septum. It was cooled down to $-15°$ C. and pentamethyl-cyclotrisiloxane-1-ol (1.70 g, 7.57 mmol) was added slowly over a 30 min period. The system was allowed to react at $-15°$ C. for 5 hours followed by 4 days at RT after which $Et_3N$ (1.5 mL, 10.8 mmol), phenyldimethylchlorosilane (1.5 mL, 9.07 mmol), and 3 mL THF were added to end cap the polymer. After 24 hours, the solution was filtered and the ammonium salt discarded. The volatiles were evaporated under vacuum and the polymer was precipitated three times from $Et_2O$/MeOH. Yield 1.72 g, (63.3%). $M_w/M_n$=32,020/11,320 (GPC), $M_W/M_n$=62,980/13,240 (Light Scattering). Tg=$-98°$ C., $T_m$=$-56°$ C. $^1$H NMR δ: 0.13 (m, 15.8H), 0.37 (m, 5.2H), 7.29(s, 2.6H), 7.56(s, 0.9H), 7.59(s, 0.8H). $^{13}$C NMR δ: −2.01(m), 0.80(m), 1.20(m), 127.97, 129.57, 129.60, 133.21, 133.27, 133.29, 139.41, 139.44, 139.64, 139.68. $^{29}$Si NMR δ: −67.78, −67.34, −67.25, −66.29, −65.86, −65.79, −21.73, −21.58, −21.53, −21.37, −21.34, −20.53, −8.29, −8.15, −2.25, −2.12, −1.76, −1.62, IR v: 3091, 3072, 3053, 3025, 3012, 2963, 2905, 1592, 1488, 1429, 1412, 1261, 1120, 1090, 1027, 999, 857, 831, 800, 755, 726, 699, 668 $cm^{-1}$. TGA: 95% left at $437°$ C. 50% left at $576°$ C. After $600°$ C., 25% residue remains.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1. Rebrov, E. A; Vasilenko, N. G; Muzafarov, A. M; et al; Polym. Preprints, (1998) 39(1), 479, 481, 581.
2. Kazakova, V; Myakushev, V; Strelkova, T; Muzafarov, A;. Preprints, (1998) 39(1), 483.
3. Herzig, C; Deubzer, B; Polym Preprints, (1998) 39(1), 477.
4. Uchida, H; Kabe, Y; Yoshino, K; Kawamata, A; Tsumuraya, T; Masamune, S; J. Am. Chem. Soc. (1990) 112, 7077.
5. Rebrov, E. A; Muzafarov, A. M; Papkov, V. S; Zhdanov, A. A; Dokl. Akad. Nauk. SSSR, (1989). 309(2), 367.
6. Morikawa, A; Kakimoto, M; Imai, Y; Macromolecules, (1991) 24(12), 3469.
7. Harris, G. I., J. Chem. Soc. (1963), 5978.
8. Battjes, K.; Kuo, C–M.; Miller, R. L.; Saam, J. C. Macromolecules (1995), 28, 790.
9. Masatoshi, A.; Sato, S. Jpn. Patent JP 61,167,694 [86, 167,694], (1986), CA 106: P 102 803 p, (1987).

What is claimed is:

1. A cyclotrisiloxane of the formula (I)

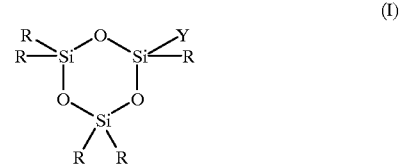

wherein Y is $OSi(R)_2H$, $OSi(R)_2OH$, or $O—Si(R)_2—OSi(R)_2—CH=CH_2$, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted.

2. The compound according to claim 1 wherein each of the R-substituents in formula (I) is the same and is an alkyl of 1 to 4 carbon atoms.

3. The compound according to claim 2 wherein each of the R-substituents is methyl.

4. A method for the preparation of a hyperbranched siloxane polymer, wherein a compound of formula (II)

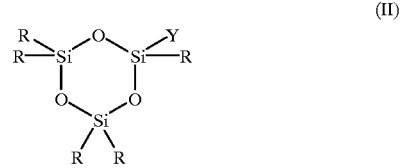

wherein Y is OH or $OSi(R)_2OH$, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted is subjected to anionic polymerization, in bulk or in a suitable solvent, to give a hyperbranched polymer, which has the formula (IIIa1, IIIa2, IIIa3) or (IIIb1, IIIb2, IIIb3)

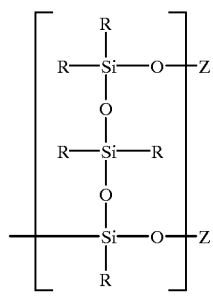

IIIa1

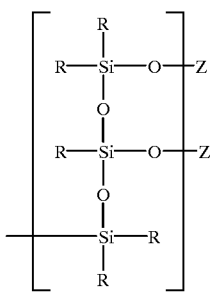

IIIa2

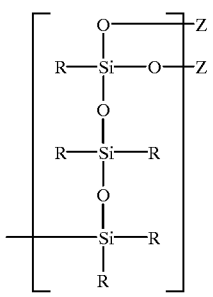

IIIa3

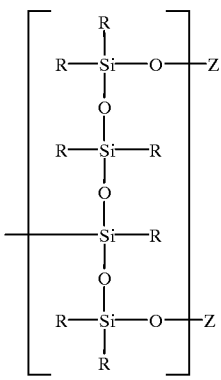

IIIb1

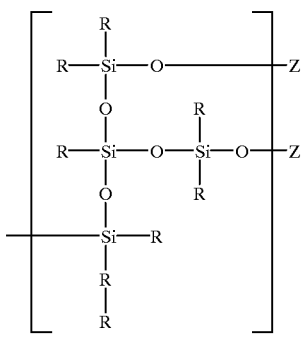

IIIb2

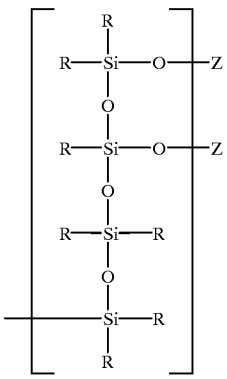

IIIb3 wherein the substituents R are as defined above and where each Z in IIIa1–a3 is one of the groups IIIa1–a3, and each Z in IIIb1–b3 is one of the groups IIIb1–b3, or Z is an endcapping group, which is the same or different, and which is hydrogen or a radical derived from a halosilane or a halosiloxane, wherein said halosilane or halosiloxane can bear finctional or non-functional groups.

5. The method according to claim 4 wherein compound (II) is subjected to a lithium containing base.

6. The method according to claim 5 wherein the lithium containing base is an alkyl lithium such as n-butyl lithium or triphenylmethyl lithium, or lithium diisopropyl amide.

7. The method according to claim 4 wherein compound (II) is subjected to a superbase.

8. A hyperbranched siloxane derived polymer of formula (IIIa1, IIIa2, IIIa3) or (IIIb1, IIIb2, IIIb3)

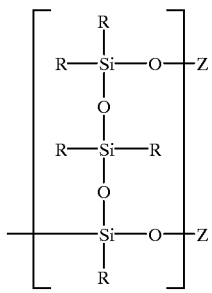

IIIa1

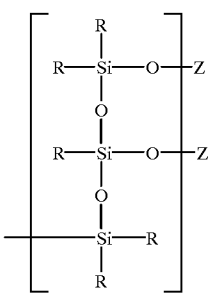

IIIa2

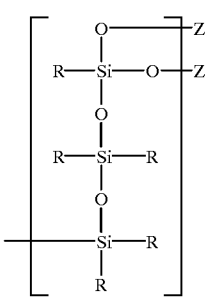

IIIa3

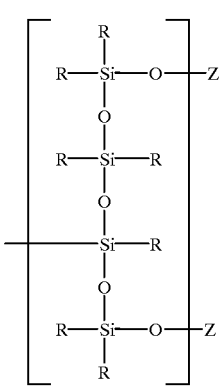

IIIb1

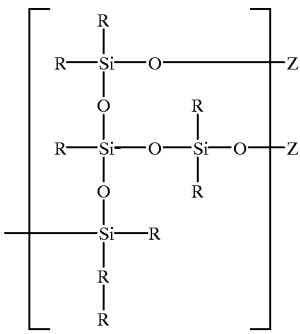

IIIb2

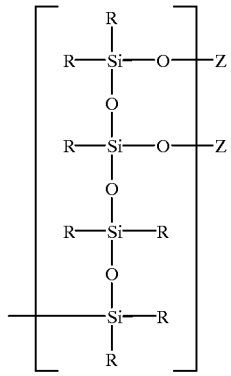

IIIb3 wherein the substituents R as well as Z are as defined in claim 4.

9. A method for the preparation of a linear siloxane polymer, wherein a compound of the formula (IV)

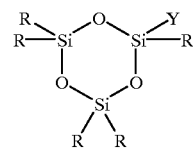

(IV)

wherein Y is O—Si(R)$_2$—OSi(R)$_2$—CH=CH$_2$, and the R substituents can be the same or different, any R substituent being selected from the group consisting of phenyl, an unsubstituted or substituted alkyl of 1 to 6 carbon atoms, wherein the optional substituent is a phenyl or one or more fluoro atoms, provided that the alpha or beta position of the alkyl chain cannot be fluorosubstituted, is subjected to cationic or anionic polymerization to give a linear polymer, which has the formula (V)

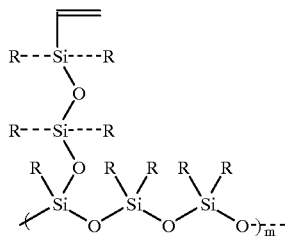
(V)

wherein the substituents R are the same as in compound (IV) and m is 3 to 9000.

10. The process according to claim 9 wherein the polymerization is a cationic polymerization initiated by trifluoromethane sulfonic acid (triflic acid).

11. The process according to claim 9 wherein the polymerization is an anionic polymerization initiated by dilithium diphenylsilanolate.

12. A linear siloxane polymer of the formula (V)

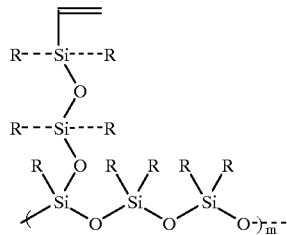
(V)

wherein the substituents R are the same as in compound (IV) and m is 3 to 9000.

* * * * *

UNITED STATES PATENT AND TRADEMARK OFFICE
CERTIFICATE OF CORRECTION

PATENT NO.    : 6,284,906 B1
DATED         : September 4, 2001
INVENTOR(S)   : Jyri Kalevi Paulasaari and William P. Weber It is certified that error appears in the above-identified patent and that said Letters Patent is hereby corrected as shown below:

Column 4,
Line 20, change "Si——Hterminated" to -- Si——H terminated --;
Line 35, delete "continued"; and
Lines 37-50, replace the formula with the following formula:

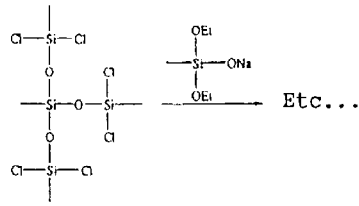

Column 6,
Lines 30-35, replace the diagonal arrow with the following:

Signed and Sealed this

Fifteenth Day of July, 2003

JAMES E. ROGAN
*Director of the United States Patent and Trademark Office*